United States Patent
Yeates

(10) Patent No.: US 12,022,936 B2
(45) Date of Patent: Jul. 2, 2024

(54) HANDHELD COSMETIC DEVICE WITH KINEMATIC AND OPTICAL SENSING FOR CUSTOMIZING TREATMENT ROUTINES

(71) Applicant: L'OREAL, Paris (FR)

(72) Inventor: Kyle Harris Yeates, Redmond, WA (US)

(73) Assignee: L'OREAL, Paris (FR)

( * ) Notice: Subject to any disclaimer, the term of this patent is extended or adjusted under 35 U.S.C. 154(b) by 710 days.

(21) Appl. No.: 17/106,840

(22) Filed: Nov. 30, 2020

(65) Prior Publication Data

US 2022/0167736 A1    Jun. 2, 2022

(51) Int. Cl.
| | |
|---|---|
| *A46B 13/02* | (2006.01) |
| *A46B 15/00* | (2006.01) |
| *A61B 34/20* | (2016.01) |
| *A61H 7/00* | (2006.01) |
| *A61B 90/00* | (2016.01) |

(52) U.S. Cl.
CPC .......... *A46B 15/0016* (2013.01); *A46B 13/02* (2013.01); *A46B 15/0006* (2013.01); *A46B 15/0012* (2013.01); *A46B 15/0036* (2013.01); *A61B 34/20* (2016.02); *A61H 7/005* (2013.01); *A46B 2200/1006* (2013.01); *A46B 2200/102* (2013.01); *A61B 2034/2055* (2016.02); *A61B 2090/065* (2016.02); *A61B 2090/3937* (2016.02); *A61B 2562/0219* (2013.01); *A61H 2201/5058* (2013.01); *A61H 2205/022* (2013.01)

(58) Field of Classification Search
CPC ............ A46B 15/0006; A46B 15/0012; A46B 15/0016; A46B 15/0036; A46B 13/02; A61B 34/20; A61H 2201/5058
See application file for complete search history.

(56) References Cited

U.S. PATENT DOCUMENTS

| | | | |
|---|---|---|---|
| 10,071,233 B2 | 9/2018 | Casasanta, III et al. | |
| 11,647,944 B2* | 5/2023 | Oh ........................ | G16H 50/20 |
| | | | 600/306 |
| 2017/0095070 A1 | 4/2017 | Machiorlette et al. | |
| 2017/0332850 A1 | 11/2017 | Powell et al. | |
| 2017/0367471 A1* | 12/2017 | Straka ................ | A46B 15/0044 |
| 2020/0033448 A1* | 1/2020 | Bourquin .............. | G01S 7/4816 |

(Continued)

FOREIGN PATENT DOCUMENTS

| | | |
|---|---|---|
| CN | 106235931 A | 12/2016 |
| CN | 106618331 A | 5/2017 |

(Continued)

OTHER PUBLICATIONS

French Preliminary Search Report and Written Opinion issued Nov. 2, 2021 in French Patent Application No. 2102456 (with English translation of Category of Cited Documents), 10 pages.

*Primary Examiner* — Timothy A Stanis
(74) *Attorney, Agent, or Firm* — CHRISTENSEN O'CONNOR JOHNSON KINDNESS PLLC

(57) ABSTRACT

A method includes determining a position of a skincare device with respect to a body part of a user via one or more sensors on the skincare device, the skincare device configured to apply a treatment to the user's body part; obtaining a location of a target area on the body part having a condition for application of the treatment; adjusting a parameter of the skincare device according to the location of the target area and based on the condition.

19 Claims, 13 Drawing Sheets

(56) References Cited

U.S. PATENT DOCUMENTS

2020/0093254 A1    3/2020  Charraud et al.
2020/0187986 A1*  6/2020  Hsu .................... A46B 15/0036
2020/0202521 A1*  6/2020  Joyce .................. A61B 5/0077

FOREIGN PATENT DOCUMENTS

| CN | 109512303 A | 3/2019 |
| --- | --- | --- |
| EP | 3 769 644 A1 | 1/2021 |
| FR | 2 962 025 A1 | 1/2012 |

* cited by examiner

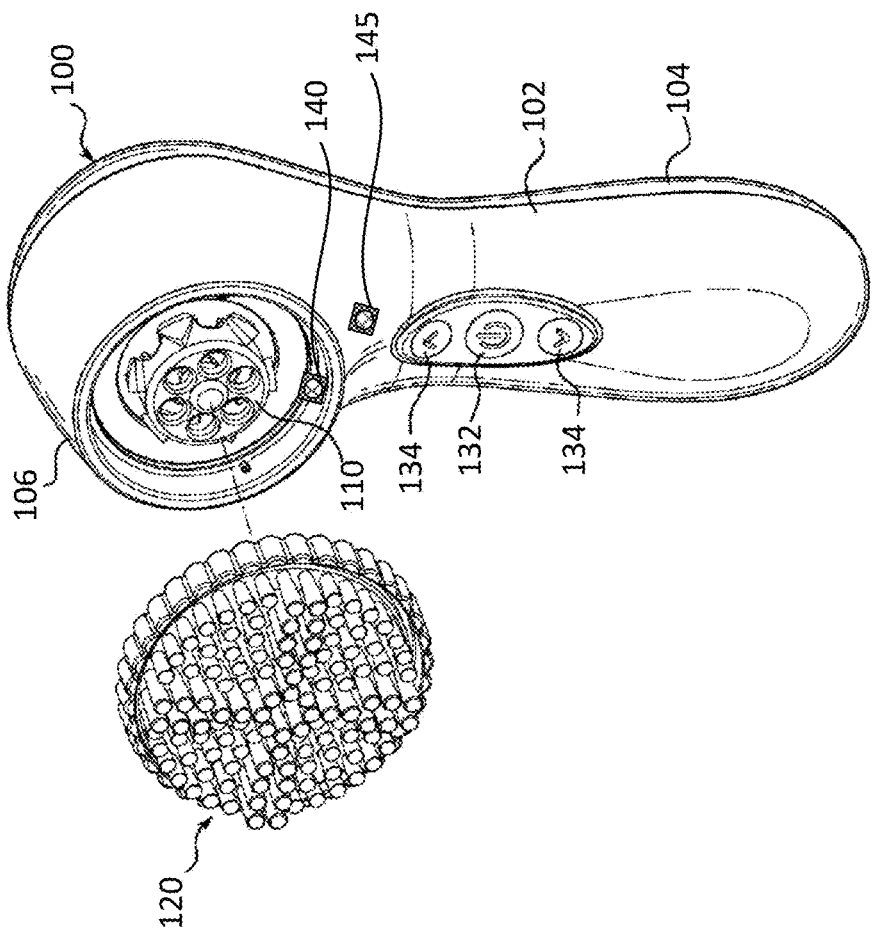
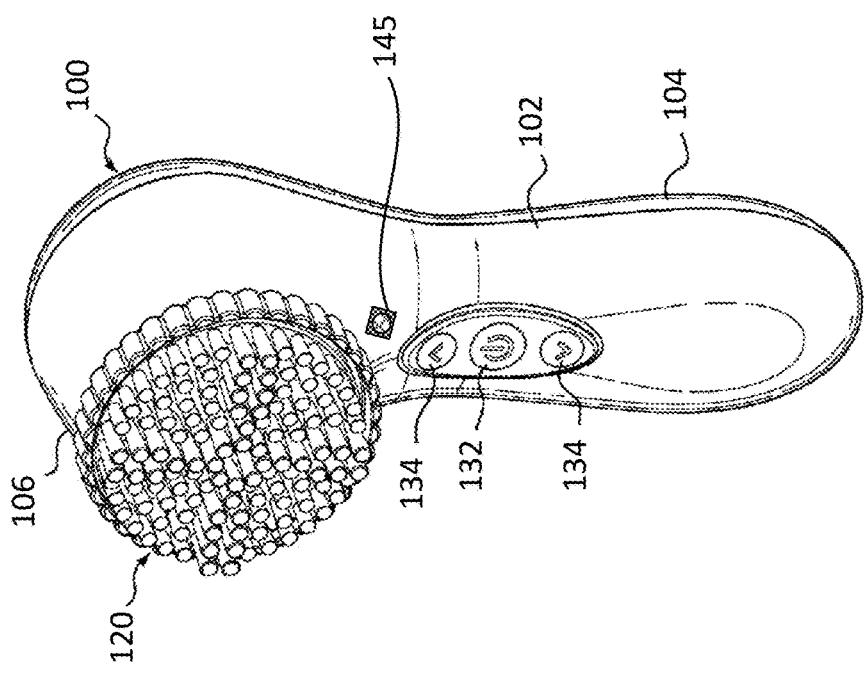

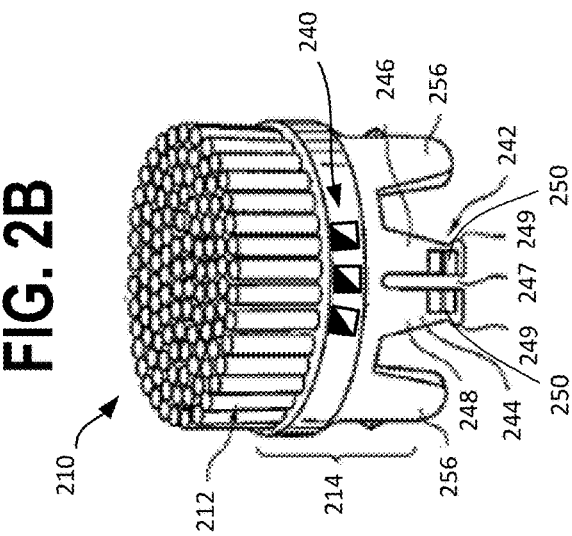
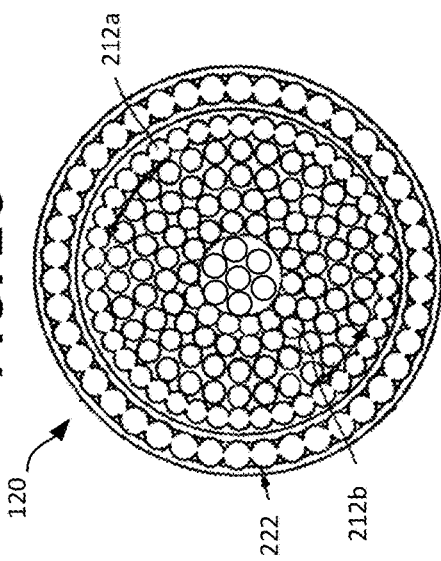
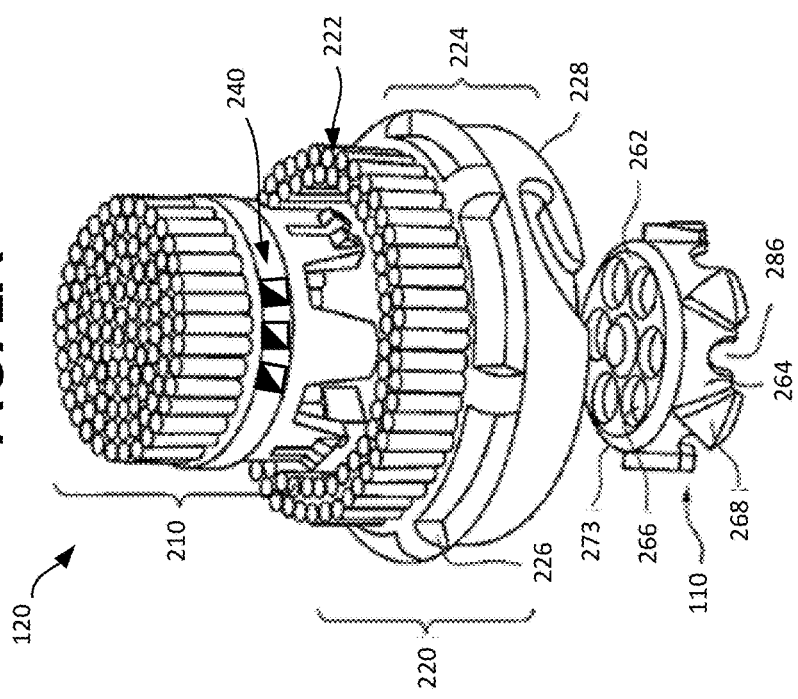

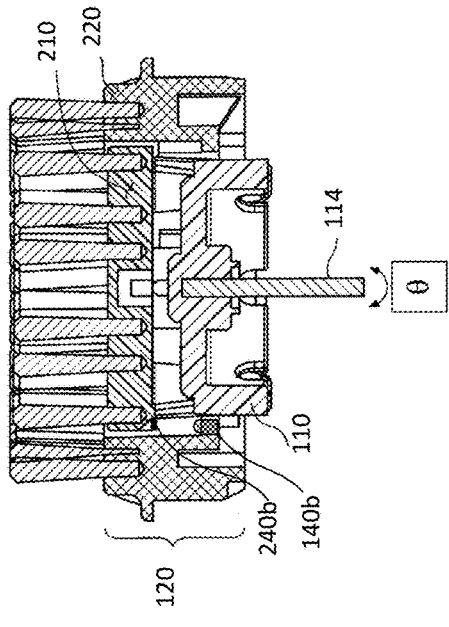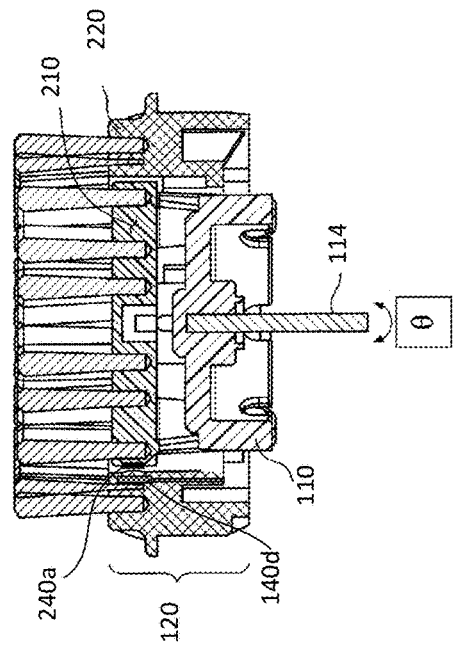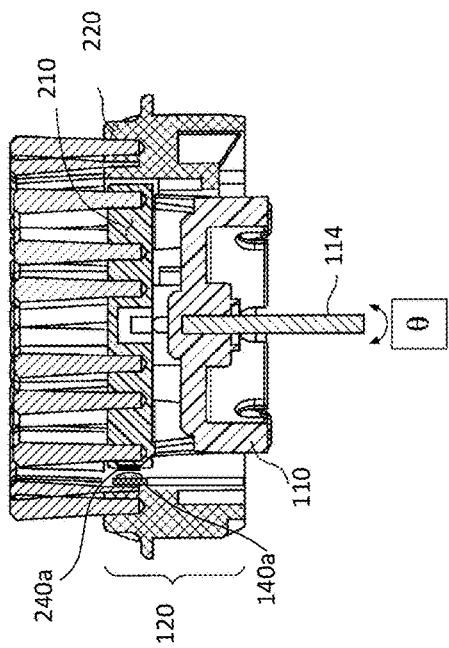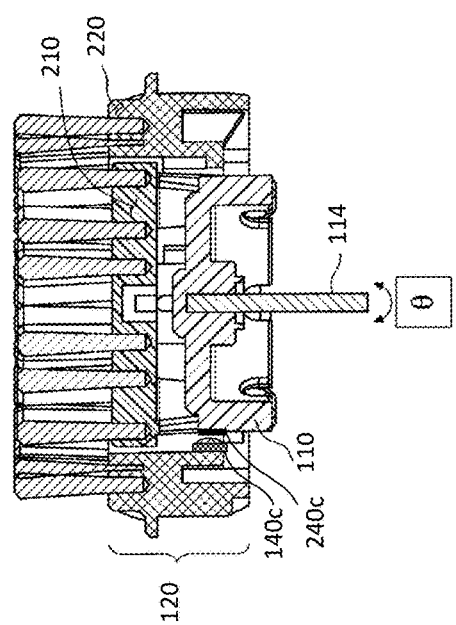

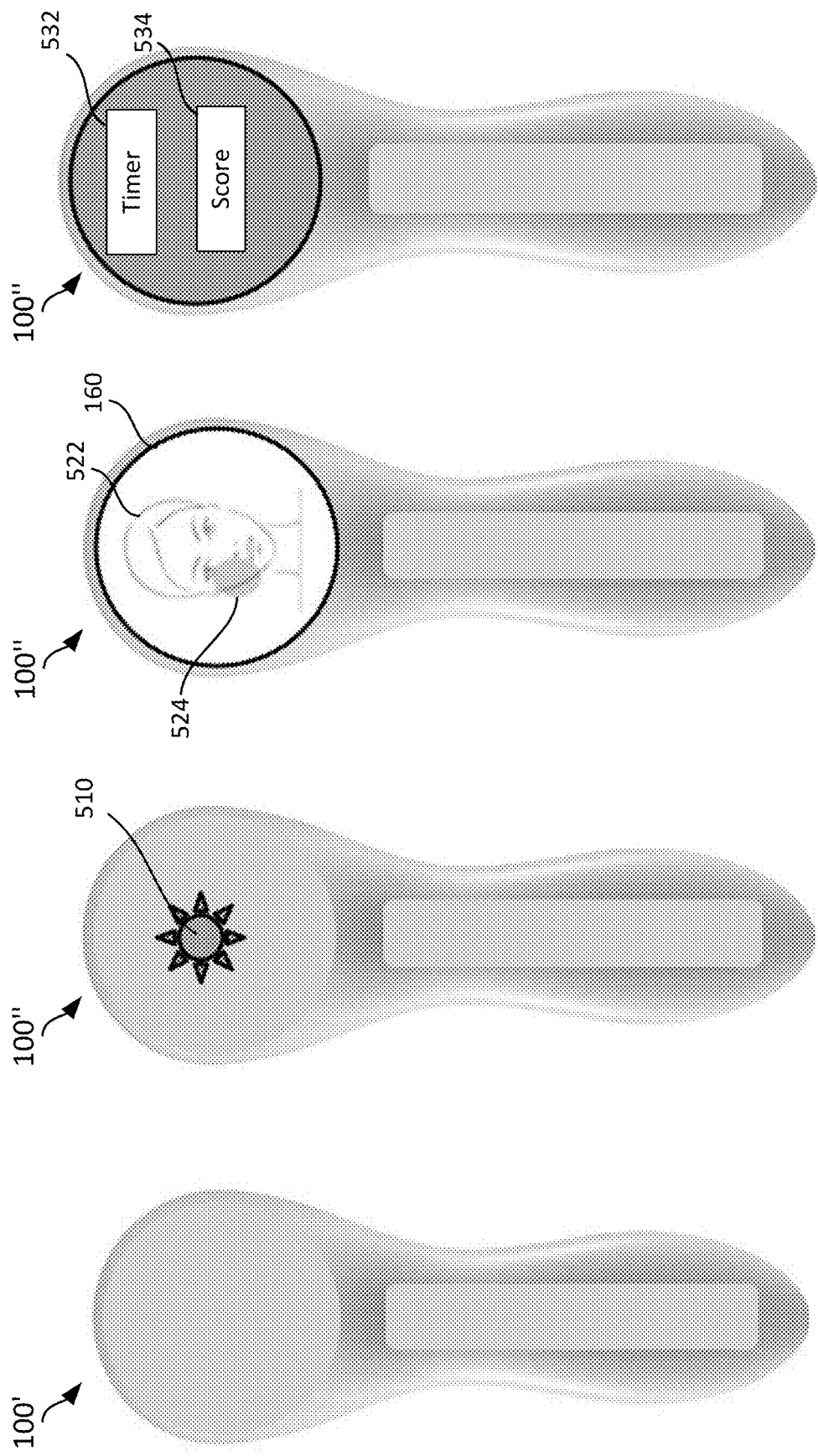

650

HANDHELD COSMETIC DEVICE WITH KINEMATIC AND OPTICAL SENSING FOR CUSTOMIZING TREATMENT ROUTINES

BACKGROUND

Field of the Invention

The application generally relates to a personal skincare device for use with brushheads, the device including a kinematic and optical sensor for detecting user-applied forces, device articulation and movement, and brushhead fiducial markers. The skincare device can adjust a parameter of the device to customize and optimize treatment of a user's skin.

SUMMARY

The present disclosure relates a skincare device, including a brushhead; a body including a motor assembly configured to oscillate the brushhead and an inertial measuring unit (IMU) configured to determine kinematic measurements of the device; a first optical encoder including a light source and an optical sensor configured to capture images; and processing circuitry configured to determine a location of the brushhead with respect to a body part of the user based on a combination of data measured from the IMU and the first optical encoder.

The present disclosure additionally relates to a method, including obtaining, via a first sensor of a skincare device, a plurality of images of a body part of a user; obtaining, via a second sensor of the skincare device, position, velocity, and acceleration measurements of the skincare device; and determining, via the first sensor and the second sensor, a position of a skincare device with respect to a body part of a user.

The present disclosure additionally relates to a skincare device, including a brushhead including a marking disposed on a surface of the brushhead, the marking including a shape and a color; a body including a motor assembly configured to oscillate the brushhead; and a first optical encoder configured to detect the marking and determine an identity of the brushhead.

The present disclosure additionally relates to a method, including detecting, via a first optical encoder disposed on a body of a skincare device, a marking disposed on a surface of a brushhead, the marking including a shape and a color, the body including a motor assembly configured to oscillate the brushhead; and determining an identity of the brushhead based on the marking.

The present disclosure additionally relates to a method, including determining a position of a skincare device with respect to a body part of a user via one or more sensors on the skincare device, the skincare device configured to apply a treatment to the user's body part; obtaining a location of a target area on the body part having a condition for application of the treatment; adjusting a parameter of the skincare device according to the location of the target area and based on the condition The present disclosure additionally relates to a skincare device, including a brushhead; a body including a motor assembly configured to oscillate the brushhead; one or more sensors configured to determine a location of the brushhead relative to a body part of the user; and processing circuitry configured to determine a position of the skincare device with respect to a body part of a user via the one or more sensors on the skincare device, the skincare device configured to apply a treatment to the user's body part; obtain a location of a target area on the body part having a condition for application of the treatment; and adjust a parameter of the skincare device according to the location of the target area and based on the condition.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIGS. 1A-1B are perspective drawings of a skincare device having a brushhead and optical encoders, according to an embodiment of the present disclosure.

FIG. 2A is a perspective view of a brushhead attachment mechanism including a drive hub of a device and the brushhead divided into an outer brushhead portion and an inner brushhead portion, according to an embodiment of the present disclosure.

FIG. 2B is a perspective view of the inner brushhead portion having a marking, according to an embodiment of the present disclosure.

FIG. 2C is a top view of the brushhead portion, according to an embodiment of the present disclosure.

FIGS. 2D-2G are graphics showing an orientation of the brush encoder detecting the marking, according to an embodiment of the present disclosure.

FIG. 5A is a schematic of a backside of the device, according to an embodiment of the present disclosure.

FIG. 5B is a schematic of the backside of the device including an indicator, according to an embodiment of the present disclosure.

FIG. 5C is a schematic of the backside of the device including a display, according to an embodiment of the present disclosure.

FIG. 5D is a schematic of the backside of the device including a timer and a score, according to an embodiment of the present disclosure.

DETAILED DESCRIPTION

Figure 1C:
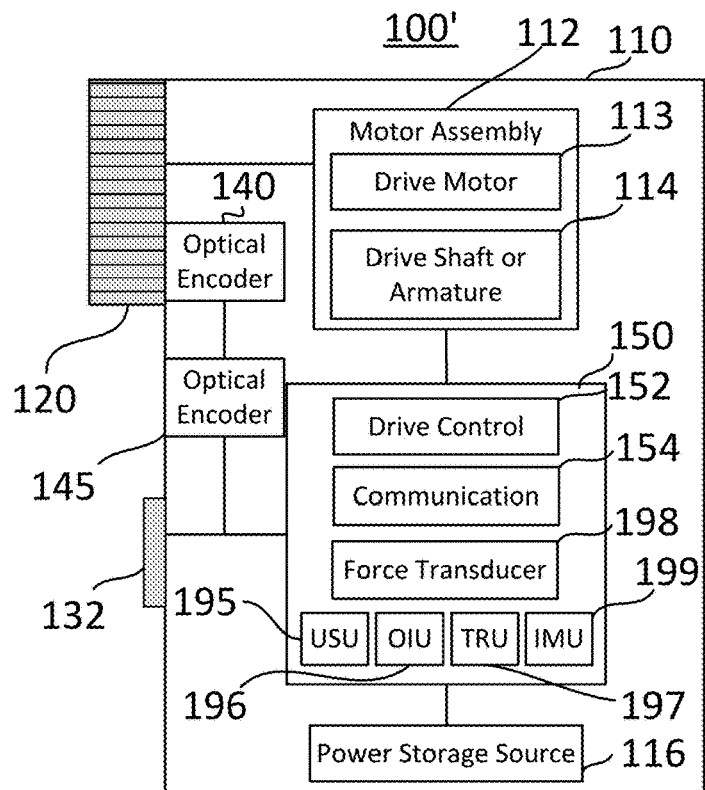
FIGS. 1C-1D are cross-sectional schematics of a device, according to an embodiment of the present disclosure.

FIG. 1A and FIG. 1B show perspective drawings of a personal skincare device 100 (herein referred to as "device 100"), according to an embodiment of the present disclosure. The device 100 includes a body 102 having a handle portion 104 and a head attachment portion 106. The head attachment portion 106 is configured to removably attach a head, such as brushhead 120, to the device 100. As shown in FIG. 1B, the device 100 includes a first optical encoder 140 and a second optical encoder 145.

The body 102 houses an operating structure of the device 100. As shown in a block diagram form in FIG. 1C, the operating structure in one embodiment includes a motor assembly 112, a power storage source 116, such as a rechargeable battery, and a controller 150. The controller 150 includes a drive control 152 and a communication part 154. In an embodiment, the controller 150 can be controlled by on/off button 132 configured and arranged to selectively connect power from the power storage source 116 to the motor assembly 112. The power storage source 116 can be charged by power delivered by a cable connected to the device (not shown). In an alternative embodiment the power storage source 116 can be charged by any wireless means including by pLink charging system, inductive Qi charging system and AirFuel. A wireless charging status can be shown as an indicator on the device or on a central device, such as a dock.

Figure 6A:
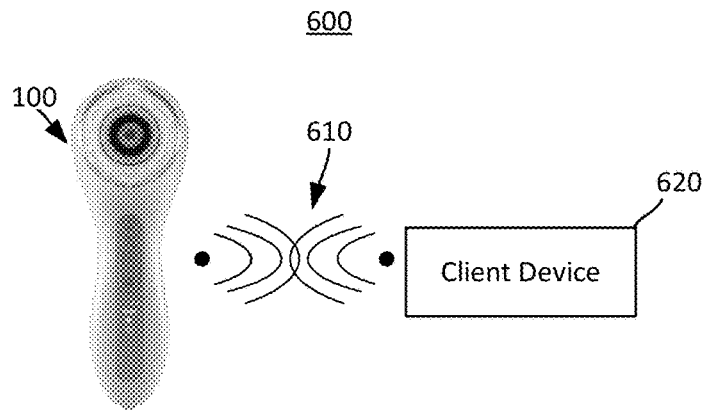
FIG. 6A is a schematic of a system to customize performance of the device including the device in communication with a central device, according to an embodiment of the present disclosure.
Figure 6B:
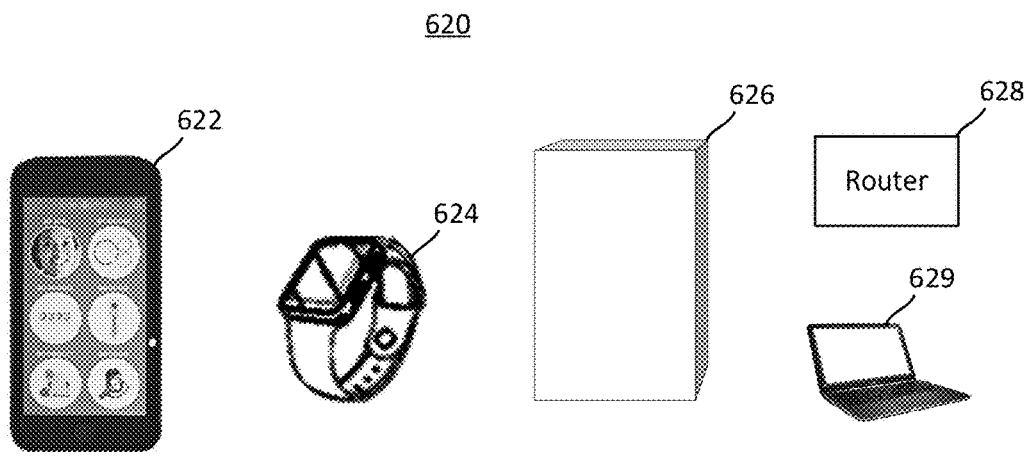
FIG. 6B is a schematic of different examples of the central device including a mobile device, a wearable electronic, a television or magic mirror, a personal computer, and a network router, according to an embodiment of the present disclosure.

In an example the communication part 154 can include circuitry and hardware for communication with a central device 620 (See FIGS. 6A-6B). In an example the communication part 154, or optionally the drive control 152, can include circuitry and hardware for communication with an alert part, an indicator, or a display 160 (See FIGS. 1D and 5B-D). The communication part 154 can include a CPU, a I/O interface, and a network controller such as BCM43342 Wi-Fi, Frequency Modulation, and Bluetooth combination, for interfacing with a network. The hardware can be designed for reduced size. For example, the CPU may be an APL0778 from Apple Inc., or may be other processor types that would be recognized by one of ordinary skill in the art. Alternatively, the CPU may be implemented on an FPGA, ASIC, PLD or using discrete logic circuits, as one of ordinary skill in the art would recognize. Further, the CPU may be implemented as multiple processors cooperatively working in parallel to perform the instructions of the inventive processes described above.

In some embodiments, the controller 150 includes a programmed microcontroller or processor, which is configured to control the oscillation of the brushhead by delivery of power to the motor assembly 112. In an embodiment, either the drive control 152 or the communication part 154 can include the CPU, memory and store a usage of each brushhead uniquely and by the type of brushhead according to an example. The controller 150 further includes an inertial measurement unit (IMU) 199 configured to track movement of the device 100. The IMU 199 measures and reports a specific force, angular rate, and orientation of an object or body using, for example, accelerometers, gyroscopes, magnetometers, or any combination thereof. The controller further includes a force transducer 198 configured to measure a force applied to the device 100. In general, force sensors and force transducers, such as the force transducer 198, measure static and dynamic tensile and compressive loads using strain gauge or piezoelectric sensors.

The motor assembly 112 in some embodiments includes an electric drive motor 113 that drives an attached head, such as the brushhead 120, via a drive shaft or armature 114. When the brushhead 120 is mounted to the head attachment portion 106, the motor assembly 112 is configured to impart motion to the brushhead 120. The motor assembly 112 may be configured to oscillate the brushhead 120 at sonic frequencies, typically in the range of 80-300 Hz, oscillating the brushhead 120 back and forth within a range or amplitude of 3-20 degrees.

The motor assembly 112 may be configured to oscillate the brushhead 120 at a natural resonance or resonant frequency as determined by:

$$2\pi \cdot F = \sqrt{\frac{K}{J}},$$

where K is a system spring rate, J is a oscillating inertia, and F is the resonant frequency in Hertz. Loading the bristles causes a change in the spring rate due to bristle bending and a change in system inertia by removing free bristle tips from an oscillating mass. The load applied to the bristles is monitored by the force transducer 198 to determine the change in the inertia.

In some embodiments, as will be described in more detail below, the brushhead 120 is operated in loaded or unloaded conditions at frequencies from about 40 Hz to 300 Hz with a range of about 3-17 degrees. In other embodiments, the brushhead 120 is operated in a loaded condition at frequencies from about 40 Hz to 300 Hz, a range or amplitude of 8-12 degrees, and a duty cycle of about 38-44%.

One example of a motor assembly 112 that may be employed by the device 100 to oscillate the brushhead 120 is shown and described in U.S. Pat. No. 7,786,626, the disclosure of which is hereby incorporated by reference in its entirety. However, it should be understood that this is merely an example of the structure and operation of one such device and that the structure, operation frequency and oscillation amplitude of such an device could be varied, depending in part on its intended application and/or characteristics of the brushhead 120, such as its inertial properties, etc. In another example, the first optical encoder 140 can be configured to track linear motion such as in is the Clarisonic Opal™ device (Clarisonic, Redmond, WA), which is described by U.S. Patent Application Publication No. 2009/0306577, incorporated herein by reference in its entirety.

In some embodiments of the present disclosure, the frequency ranges are selected so as to drive the brushhead 120 at near resonance. Thus, selected frequency ranges are dependent, in part, on the inertial properties of the brushhead 120.

It will be appreciated that driving the attached head at near resonance provides many benefits, including the ability to drive the attached head at suitable amplitudes in loaded conditions (e.g. when contacting the skin) while consuming the least amount of energy from the power storage source. For a more detailed discussion on the design parameters of the device, please see U.S. Pat. No. 7,786,626, incorporated herein by reference in its entirety.

In an embodiment, the second optical encoder 140 is configured to track the motion of the device 100 as the device 100 is manipulated across a surface, such as the skin of a user. The second optical encoder 140 includes, for example, an optoelectronic sensor and a light source (e.g. LED or IR laser) configured to successively image the surface on which the device 100 operates. Based on changes in patterns over a sequence of images, processing circuitry, such as a digital signal process (DSP), determines a distance and direction the device 100 has traveled. This can operate in conjunction with the IMU 199 to incorporate kinematic data, such as acceleration, position, velocity, angular deflection, or any combination thereof. Separately, each of the measurement systems have particular strengths, and by combining their data with a tracking process, a more robust and reliable set of kinematic data can be produced. The IMU 199 provides more accurate acceleration and velocity data (compared to the second optical encoder 145), regardless of the environment in which the device 100 is being used (wet/dry/foggy/soapy/etc.), but is less accurate in positional accuracy (compared to the second optical encoder 145) due to double integration errors when converting acceleration data to positional data. The second optical encoder 145 provides increased positional accuracy in certain conditions where the optical path is not obstructed. Additionally, optical measurement systems, such as the second optical encoder 145, can pick up on targeted areas or landmarks of the body (moles, freckles, acne, inflamed skin, rough skin, etc.).

By having accurate kinematic data, diagnoses can be improved by localizing certain conditions on a user's face or body. Furthermore, therapy can be targeted to local areas of a user's face or body where treatment would be most beneficial. This can be augmented via high resolution surface imaging and skin condition detection using the second optical encoder 140. In addition to tracking the movement of the device 100, the second optical encoder 140 can image and detect particular regions of the user's skin that may benefit from a tailored skin care regimen. For example, the device 100 can detect a region of the user's skin that can use additional exfoliation and relay this detection to the controller 150 to increase the oscillation of the brushhead 120. Similarly, in another example, the device can detect a region of the user's skin that includes sensitive acne inflammation and relays this detection to the controller 150 to decrease the oscillation of the brushhead 150. As described below, a sound, a visual alert, or a vibration or haptic feedback can be communicated to the user to adjust the applied force.

In an embodiment, the force transducer 198 is configured to detect the force applied to the device 100 by the user and relay the force information to the CPU to determine a dampening of the oscillation of the brushhead 120 due to the applied force. The applied force changes the spring rate as described above and thus changes the resonant frequency of the brushhead 120, i.e. the oscillation. Upon determining the oscillation under the applied force is less than a target resonant frequency, the processor can increase delivery of power to the motor assembly 112 and thus increase the oscillation of the brushhead 120. In conjunction with the IMU 199 and the second optical encoder 145, the detected applied force from the force transducer 198 can be used to further increase the accuracy of the target resonant frequency when it is determined that the brushhead 120 is approaching or has entered a region of the user's skin that may benefit from a change in the brushhead 120 oscillation.

In one example, the kinematic data from the IMU 199 and the second optical encoder 145 can indicate that the brushhead 120 is over a region with acne (i.e. more sensitive skin) and the processor thus reduces the oscillation of the brushhead 120. However, without the force transducer 198, the processor may not detect that the user is applying above average force to the device 100. Thus, a predetermined reduction in oscillation to the brushhead 120 for sensitive skin may not be sufficient to optimize comfort for the user as the brushhead 120 is translated across the sensitive skin. By incorporating the detected force via the force transducer 198, the processor can both detect the approaching region includes acne (via the kinematic data and/or the captured images) and that the user is applying above average force to the device 100. Upon such a determination, the processor can execute the predetermined reduction in oscillation to the brushhead 120 plus an additional second reduction to compensate for the above average applied force to bring the total oscillation down to the target resonant frequency for sensitive skin. In a converse example, the user can apply a below average force and the predetermined reduction in oscillation to the brushhead 120 can be less than the standard amount based on the below average applied force by the user that is detected by the force transducer 198.

Figure 1D:
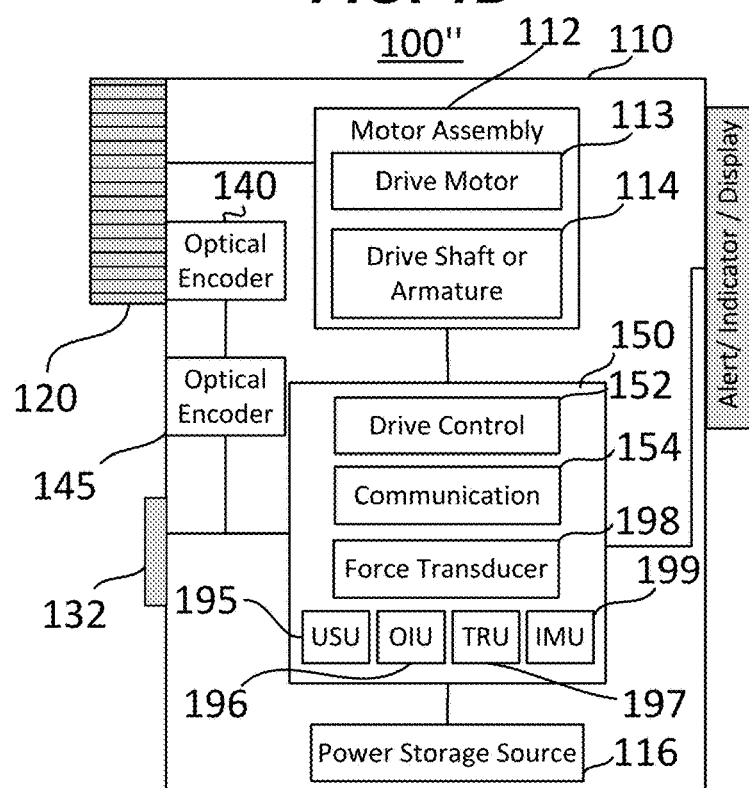

FIG. 1D shows a schematic diagram of a device 100" similar to that of device 100', further including an alert part, an indicator, or a display 160 according to an example (See FIG. 5B-5D). The alert part can be configured to give an alert to the user based on the first optical encoder 140, the controller 150, or the IMU 199. The alert can be a sound, a visual alert, or a vibration or haptic feedback. In an embodiment, the indicator and/or the display can be configured to communicate to the user, such as a routine on where and how to use the device 100" according to an example. In an embodiment, the display can be a touch display and configured to receive input from the user.

A routine can include one or more regimens, where each regimen has a set of protocols. An example of a routine includes an event date and a protocol. The routine further can include a plan for a number of sessions. The plan can be based on the event date according to an example. Each session can record a score 534 matching the protocol. An example of the score 534 can be based on multiplying the oscillation speed, pressure, and duration with each other. Myriad indexing systems for determining the score 534 can be contemplated. Other regimens besides those for the face of the user include, for example, a foot regimen, a body regimen, etc. A protocol designer can be used to define a regimen with a set of the protocols. The regimen can have a protocol name, a type of brushhead, a duration, an applied force and a series of steps including a particular skin region to apply the protocol according to an example. The aforementioned can be recorded by the device 100 to adjust or customize predetermined regimens for the user based on the user's usage of the device 100.

In an embodiment, the device 100 can include a treatment regimen unit (TRU) 197 including processing circuitry configured to vary a treatment duty cycle responsive to one or more inputs indicative of a user sensitivity, a treatment area, and a change in the real-time kinematic data when the device 100 is applied to a body part of the user. The device 100 can further include an object identification unit (OIU)

196 including processing circuitry configured to identify a treatment area location, wherein the treatment regimen unit is configured to vary the treatment duty cycle responsive to one or more inputs indicative of the user sensitivity, a treatment area identity, and a change in the real-time kinematic data measured. The device 100 can further include a user sensitivity unit (USU) 195 including a graphical user interface including one or more instances of selectable user sensitivity, the user sensitivity unit configured to receive user sensitivity information (e.g., sensitive skin area, presence or absence of acne, dry skin area, temperature sensitive area, and the like).

Next, parts of the brushhead 120 are described in different examples. Referring now to FIG. 2A, a brushhead attachment mechanism can include an inner brushhead portion 210, having a marking 240, interfacing with the drive hub 110, which oscillates through a selected angle or amplitude during operation of the device 100.

The marking 240 can be a set of fiducial marks that are detected by the first optical encoder 140. In one example, the marking 240 can be a printed shape or a set of engravings on a part of the brushhead 120. The marking 240 can be a repeating pattern of black and white shapes. The marking 240 can additionally have a thickness relative to a surface upon which the marking 240 is disposed via attaching, printing, engraving, etc. That is, the marking 240 can be formed thicker by printing over the same area multiple times to additively form a raised shape. Concomitantly, the marking 240 can be formed deeper (i.e. have a negative thickness) into the surface upon which the marking 240 is disposed by engraving deeper into the surface. After engraving, the black or white shapes can be printed onto the engraved surface. The varying heights of the shapes are detected by the first optical encoder 140 by determining the needed focal length to focus on an outline of the shape of the marking 240. In an example, the marking 240 can be a strip sized to cover a desired max angle. In an embodiment, the marking 240 can be configured to provide an identity of the brushhead 120 attached to the device 100. In an example one or more of the shapes of the marking 240 can be based on the oscillation of the brushhead 120 such that they are configured to have an aliasing effect with respect to the oscillation. For instance, when the brushhead 120 is oscillating at a specific frequency, the one or more shapes can appear to be stationary based on a sampling rate of the first optical encoder 140. A precision of the first optical encoder 140 can be based on variations of the aliasing effect of the oscillation.

The marking 240 can be used to identify a type of the brushhead such as an acne cleansing brush or a dynamic facial brush. In another embodiment the marking 240 can be used to identify the brushhead uniquely. In an example, the marking 240 can include a unique identifier such as a coded serial number separate from the set of fiducial marks. In an embodiment either the brushhead or the marking 240 can include a RFID tag and the first optical encoder 140 can be configured to detect the RFID tag and associate a usage history to the brushhead 120. The first optical encoder 140 can include an active RFID reader. The RFID reader can be used to track the position of the RFID tag in an Active Reader Active Tag (ARAT) system, for example. In an example, the usage history of the brushhead 120 is communicated to the user and used to suggest or automatically replenish the brushhead 120.

Figure 3A:
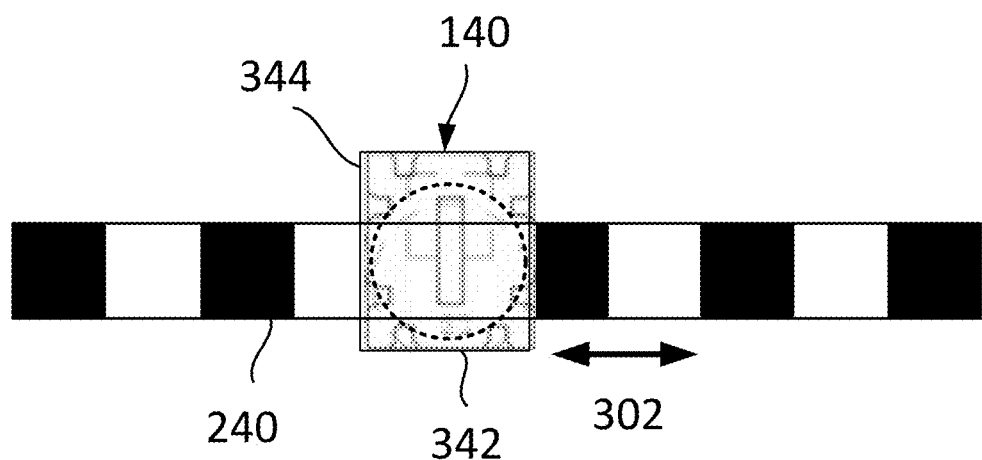
FIGS. 3A-3B show a flexible applicator tip, according to an embodiment of the present disclosure.
Figure 3B:
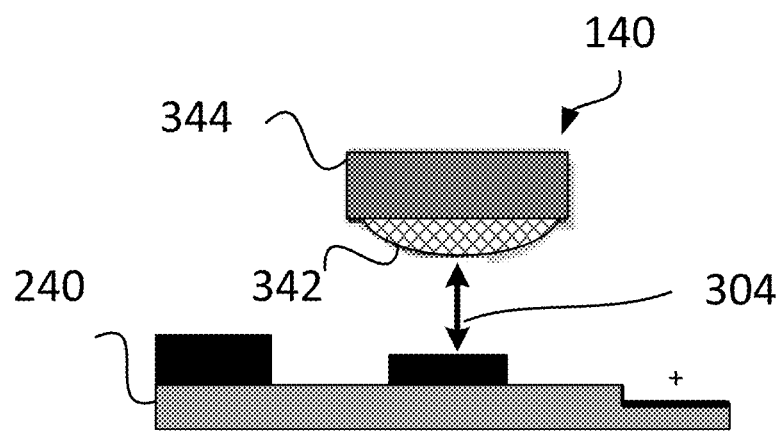

In an example shown in FIG. 3A and FIG. 3B, the marking 240 can be a line of the one or more shapes, such as squares of black and white boxes. In one example, the line of black and white boxes can be configured to have optical contrast along a single plane or at varying heights based on the printing or engraving performed to adjust the thickness of the black and white boxes. As one skilled in the art would understand, alternate complementary markings or codes, and encoders can be used with the same or different amounts of precision in detecting the shapes and their oscillation.

The first optical encoder 140 can be a 3-D camera capable of determining varying focal distances of the shapes of the marking 240 as well as the black or white pattern of each shape. The first optical encoder 140 is preferably water resistant or configured to be water resistant by packaging for wet brush loading. Alternatively, the first optical encoder 140 can be attached to the motor armature such that the first optical encoder 140 is contained within the body, making waterproofing unnecessary. In an embodiment, the first optical encoder 140 can detect the marking 240 with non-optical light such are IR, LASER, or LIDAR.

Returning to FIG. 2A, the brushhead 120 optionally can include an outer brushhead portion 220, which remains stationary during operation of the device 100. In an embodiment shown in FIG. 2A and FIG. 2C, a row(s) of bristle tufts are circular and move in an arcuate manner with an axis of rotation perpendicular to a surface of the skin. FIG. 2A and FIG. 2C show an embodiment in which a set of rows 212 move and an optional set of rows 222 are fixed.

The inner brushhead portion 210 has an operative relationship with the drive hub 110 such that as the drive hub 110 oscillates through a selected angle, so does the inner brushhead portion 210. The outer brushhead portion 220 includes a central, cylindrically shaped opening. The central opening is sized and configured to surround the sides of the inner brushhead portion 210. When attached to the device 100, a rim, which extends around the top periphery of the central opening, is flush with or positioned slightly above the outwardly facing surface of the body 102.

In some embodiments, the inner brushhead portion 210 and the outer brushhead portion 220 together include a brushhead attachment mechanism configured to provide selective attachment of the brushhead 120 to the head attachment portion 106 of the device 100.

In the embodiment shown, the outer brushhead portion 220 is annular, with an outside diameter of approximately 1.975 inches, with a central opening. The outer brushhead portion 220 includes a base portion 224 with a rim around the top periphery thereof which includes a plurality of spaced finger grips 226, which helps the user in installation and removal of the brushhead 120. The outer brushhead portion 220 can further include a plurality of brushhead bristles 222 which extend upwardly from the base portion 224. There may be a gap or space between the bristles of the inner and outer brushhead portions, in the range of 0.050-0.125 inches, preferably 0.084 inches.

When attached to the device 100 by the brushhead attachment mechanism, the following occurs: (1) the inner brushhead portion 210 is operatively connected to the motor assembly 112, for example, via a drive hub 110, in a manner that provides oscillating motion thereto; and (2) the outer brushhead portion 220 fixedly secures the brushhead 120 to the head attachment portion 106 of the device 100.

Accordingly, the brushhead attachment mechanism in some embodiments provides a quick and easy technique for attaching and detaching the brushhead 120 to the device 100. It will be appreciated that the brushhead attachment mechanism also allows for other personal care heads to be attached to the device, and allows for a replacement brushhead 120 to be attached to the device 100, when desired. One brushhead attachment mechanism that may be practiced with embodiments of the present disclosure is set forth in U.S. Pat. No. 7,386,906, the disclosure of which is hereby incorporated by reference in its entirety.

It will be appreciated that other brushhead attachment mechanisms can be employed to provide either tooled or tool-less techniques for selectively attaching the brushhead 120 to a personal care device, such as device 100, in a manner that (1) provides oscillating motion to the inner brushhead portion 210; and (2) maintains the connection between the inner brushhead portion 210 and the motor assembly 112. For example, in some embodiments, the inner brushhead portion 210 includes a coupling interface configured to cooperatingly connect to an oscillating drive shaft or armature, such as armature 114, of an associated motor assembly 112 in a manner that transmits oscillating motion to the inner brushhead portion 210.

The above-described examples of the brushhead 120 can be used to exfoliate skin of a user's epidermis. In that regard, the brushhead 120 is first attached to the device 100. Next, if desired, a skin softening agent, such as skin care formula, can be placed on the tips of bristles of a first group of tufts 212.

FIG. 2B shows the inner brushhead portion 210 in more detail in according to an example. The inner brushhead portion 210 has a generally circular configuration and is arranged to fit into the central opening of the outer brushhead portion 220.

The inner brushhead portion 210 includes a plurality of inner brushhead bristles 212 which extend upwardly from a base portion 214, with the bristles 212 arranged in a circular pattern covering the entire upper surface of the base portion 214.

The inner brushhead portion 210 in the embodiment shown includes two sets of depending legs on the outer periphery thereof. The first set of three legs 242-242, spaced at 120° intervals, each leg having a pair of snap portions 244 and 246, defined by a slot 247 which extends down the middle of each snap leg 242.

The two snap portions of each snap leg are configured and arranged to slightly flex toward each other during installation of the inner brushhead portion 210 on the drive hub 110, with the outside edges of the free tips of the snap portions 244, 246 having outward bulges 249-249 which snap back (with the snap portions) after they pass over a pointed portion of the drive hub 110, helping to tightly engage the drive hub 110 and retain the inner brushhead portion 210 on the drive hub 110.

The inner brushhead portion 210 further includes a second trio of spaced drive legs 256-256. The drive legs 256 alternate with snap legs 242 around the periphery of inner brushhead portion 210 and are also separated by 120° intervals.

The drive legs 256 taper slightly from their base to their free ends, which are rounded, designed to provide a close tolerance fit between them and the drive hub 110.

The brushhead 120 structure and assembly is described in more detail in U.S. Pat. No. 7,386,906, which is owned by the assignee of the present application and is incorporated herein by reference in its entirety.

FIG. 2C shows a top view of the brushhead bristle arrangement according to an example. The plurality of inner brushhead bristles 212 with an outer-most row of bristles 212a. During oscillation, the outer-most row of bristles 212a will have a greater linear amplitude as compared to another row of bristles 212b, approximately according to r·θ, where r is a radius from a center of the brushhead 120 and θ is an angle of oscillation in radians.

The brushhead bristle 212 arrangement shown and described herein, used in the device/brushhead disclosed in the above applications is effective for skin cleaning applications, particularly facial skin. The present brushhead bristle 212 arrangement can also be used in other skin care applications, however, as discussed in the above applications, including acne and black head treatment, athlete's foot treatment, callused skin and psoriasis, razor bumps and related skin applications, wound cleansing and treatment of slow or non-healing wounds, scalp cleaning, chemical peel procedures and shaving cream applications. Preferred bristle configurations and arrangements will differ somewhat depending upon the particular application.

FIGS. 2D-2E show a cross-section of a brushhead (e.g. of FIG. 2A) that is positioned on the drive hub 110 and connected to the drive shaft 114. The first optical encoder 140 and the marking 240 are shown in alternate locations in each of the figures. In FIG. 2D, the marking 240a is shown located on an outer surface of the brushhead 120 facing the outer brushhead portion 220, similarly as shown in FIG. 2A and FIG. 2B. The brush encoder 140a is positioned on an extension of the device in a respective location to detect the marking 240a. In FIG. 2E, the marking 240b is shown on an underside of the inner brushhead portion 210 facing the device. The first optical encoder 140b is positioned in a respective location to detect the marking 240b. In FIG. 2F, the marking 240c is shown on a side of the drive hub 110. The first optical encoder 140c is positioned in a respective location to detect the marking 240c. In an embodiment, the first optical encoder 140 can be used to monitor a status of a part of the motor assembly 112 such as the connection between the drive hub 110 and the drive shaft 114, which is prone to wear from oscillations of many millions of cycles. In an embodiment, the first optical encoder 140 can be used to monitor a status of a part of the operating structure such as the power storage source 116 (e.g. battery). One or more markings and first optical encoders can be placed at locations to differentiate a device 100 status.

In an embodiment, the first optical encoder 140d can be integrated in an outer brushhead portion that further includes a set of electrical connections connecting the first optical encoder 140 to the operating structure or circuitry of the device 100 (See FIG. 2G). In this example, circuitry can be connections to the controller 150, the drive control 152 or the communication part 154 as in FIG. 1C and FIG. 1D. In another embodiment, the first optical encoder 140 can be integrated in an outer brushhead portion as a separate first optical encoder device (See FIG. 6C). In another embodiment, the first optical encoder 140 can be integrated into an operating structure of the device 100 such that the motion of the internal motor assembly components can be measured and correlated to the brush amplitude.

FIG. 3A and FIG. 3B are graphics showing an orientation of the first optical encoder 140 detecting the marking 240 of the brushhead 120. FIG. 3A shows the first optical encoder 140 overlapping with at least a portion of the marking 240 of the brushhead 120 according to an example. The first optical encoder 140 can have a detector part 342 for sensing and a circuitry part 344 for processing and/or transmitting. In FIG. 3A, an outline of the detector part 342 is shown as a dotted circle. In an example, a lens can be further included for enhancing optics of the detector part 342. The line of black and white shapes of the marking 240 can have a spacing 302.

FIG. 3B shows a side view of an orientation of the first optical encoder 140 detecting the marking 240 of the brushhead 120, exposing a gap 304 between the first optical encoder 140 and the marking 240 of the brushhead 120 according to an example. Here the detector part 342 is shown. When in use, either circuitry of the device or the circuitry part 344 detects the shape and optionally the thickness/height of the shape and sends out a signal or digital quadrature signal, or similar in function or purpose, a translated waveform encoding the shape and oscillation.

In an example, the first optical encoder 140 or the operating structure or circuitry of the device 100 can calculate a degree per count (DPC) based on detection of the marking 240 over time. The DPC can be calculated by an equation:

$$DCP = \frac{360°}{LPI \cdot IF \cdot C}$$

where LPI is the lines or shapes per inch, IF is an interpolation factor, and C is a circumference of the brushhead. The interpolation factor can account for interpolation between shapes which may be performed by the first optical encoder 140 to enhance position resolution.

Figure 4A:
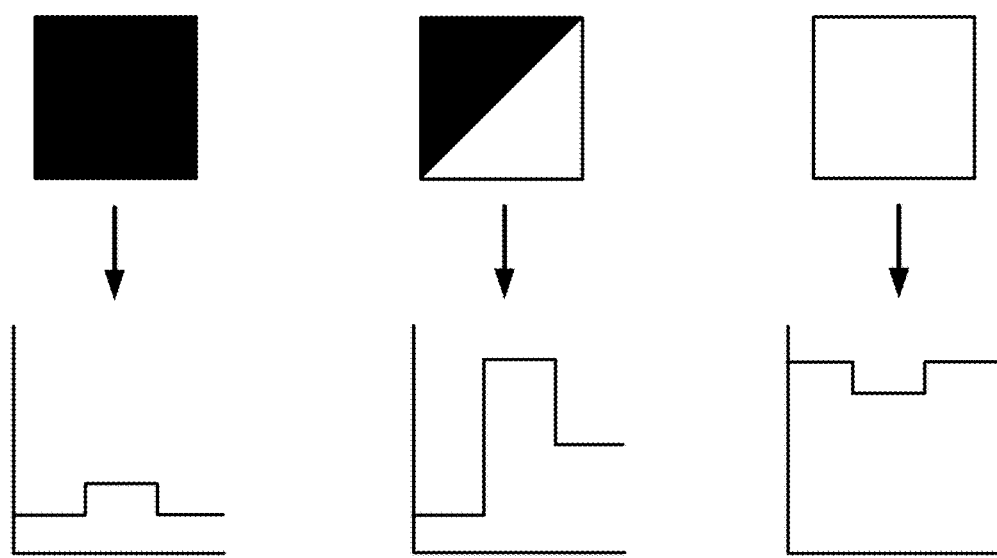
FIG. 4A is a schematic representing signals generated by the optical encoder detecting various markings, according to an embodiment of the present disclosure.

FIG. 4A shows a graphic representing the signal or waveform generated by the first optical encoder 140 according to an example. Based on the black and white pattern of the shape of the marking 240, varying waveforms can be generated to identify the brushhead 120. This can be coupled with the varying thickness of each shape that is detected by the first optical encoder 140 via determining the focal length to the surface of the shape (i.e. via adjusting the focus of the first optical encoder 140 to bring the shape into focus, and thus determining the thickness of the shape).

Figure 4B:
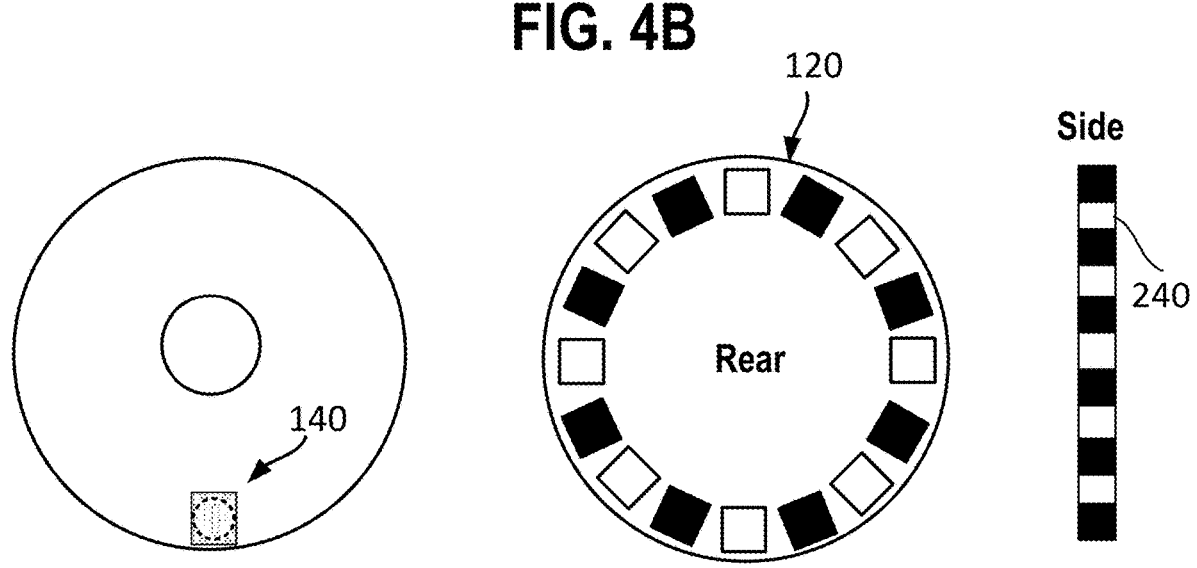
FIG. 4B is a schematic of the marking arranged in various locations on the brushhead and an optical encoder arranged on the device, according to an embodiment of the present disclosure.

FIG. 4B shows a graphic representing the first optical encoder 140 disposed on the device 100 and the one or more shapes on the brushhead 120 according to an example. According to certain embodiments, the marking 240 can be a ring of the one or more shapes that is disposed on the back of the brushhead 120 opposite the surface having the bristles 212 (center of FIG. 4B). This ring of the marking 240 can be detected by the first optical encoder 140 disposed on a surface opposite the back of the brushhead 120, as shown in FIG. 1B as well as the left schematic in FIG. 4B. In certain embodiments, the ring of the marking 240 can be disposed along an edge of the brushhead 120 as shown in FIGS. 2D, 2F, and 2G, as well as the right schematic in FIG. 4B.

FIGS. 5A-5D show drawings of alternate examples of a backside of the device 100. According to different embodiments, the device 100 can have one or more indicators and displays 160. FIG. 5A shows an embodiment of the backside of the device 100' having no additional features. FIG. 5B shows an example of the backside of the device 100" having at least one indicator 510. Each indicator 510 can have one or more LEDs or light emitting colors and shapes which can be configured to indicate triggering of the alarm. FIG. 5C shows an example of the backside of the device 100" having a display 160. In one example, the display 160 can be a digital screen such as an LCD configured to play videos and tutorials and demonstrate a method of use of the device 100" and highlight a target area 524. In another example the display 160 can be a fixed graphic 522 with an indicator 524 illuminating a different part of the fixed graphic 522. In an embodiment, the display 160 can be configured to show a reverse image such that an image or graphic will appear correctly in a mirror during use.

FIG. 5D shows an embodiment of the backside of the device 100" having the indicator or display as a timer 532 and/or a score 534. Here, the indicator can be made of one or more seven-segment displays (SSD), or seven-segment indicators for displaying decimal numerals. The timer 532 and the score 534 can correspond with the protocol according to an example. For instance, the timer 532 can correspond with a protocol duration of the target profile. In an embodiment, the timer 532 and the score 534 can be configured to show a reverse ordering such that they will appear in a correct ordering in a mirror during use.

FIG. 6A shows a system 600 to promote an optimal performance of the device including the device 100 in communication with a central device 620 according to an example. In one example, the system 600 can include the device 100 in communication with the central device 620 with a wireless signal 610. The central device 620 can be configured to operate a software application or set of software modules to receive and send communications from and to the device 100. In an example, the software application can send a protocol or target profile to the device 100, as well as receive data from the brush encoder to track the usage in realtime.

FIG. 6B shows different examples of the central devices 620 including, a mobile device 622, a wearable electronic 624, a television or magic mirror 626, a network router 628, and a personal computer 629. The wireless signal 610 can be any appropriate signal such as an electromagnetic signal including WIFI, Bluetooth, near-field, or any other signal such as optical, and acoustic. Each client device, including the device 100, may communicate with each other through an internet connection via an 802.11 wireless connection to a wireless internet access point, or a physical connection to the internet access point, such as through an Ethernet interface. Each connected device is capable of performing wireless communication with other devices, such as through a Bluetooth connection or other wireless means as well.

Figure 6C:
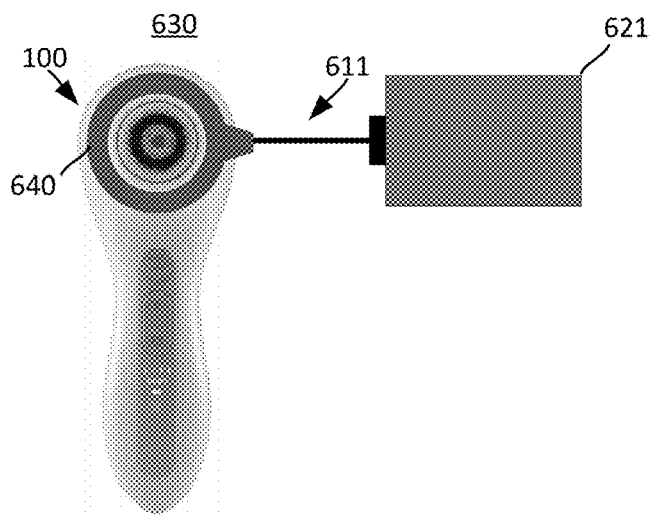
FIG. 6C is a schematic of a system including a brush encoder device including an outer brushhead portion having the optical encoder and a peripheral device configured for optical encoder processing, according to an embodiment of the present disclosure.

FIG. 6C shows a system 630 including a brush encoder device 640 including an outer brushhead portion having the first optical encoder 140 and a peripheral device 621 configured for encoder processing according to an example. The brush encoder device 640 can be connected to the peripheral device 621 by a wireless signal 610 or a wired connection 611. The brush encoder device 640 can be interchanged and removably attached to different devices such that a series of devices can be tested with the same first optical encoder such as for manufacturing use. Accordingly, the peripheral device 621 can be configured to monitor and to test manufacturing and production of a part of the device 100. The peripheral device 621 can be a computer or a data acquisition device (DAQ) such as mBed LPC1768, and can further connect to a computer operating data acquisition software or other peripheral device. In an embodiment, the brush encoder device 640 can be used to test other embodiments of the devices described here, as well as embodiments of devices without the first optical encoder.

Figure 6D:
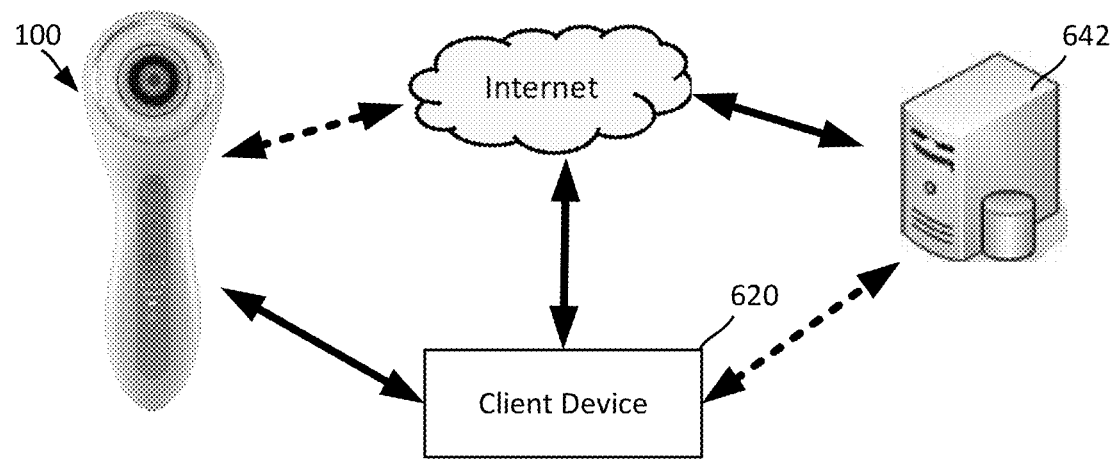
FIG. 6D is a diagram of a system to customize performance of a skincare device, according to an embodiment of the present disclosure.

FIG. 6D is a diagram representing an example of a system to promote optimum performance of a personal skincare care device 650, according to one example. The system 650 includes at least the device 100 and the peripheral device. Optionally, the system 650 may further include one or more external servers 642 which are implemented as part of a cloud-computing environment and in communication with the system 650 through the Internet. The one or more external servers 642 can store user data, products such as brushheads and formulations, protocols and routines, tutorials, as well as other $3^{rd}$ party services according to an example.

Figure 7A:
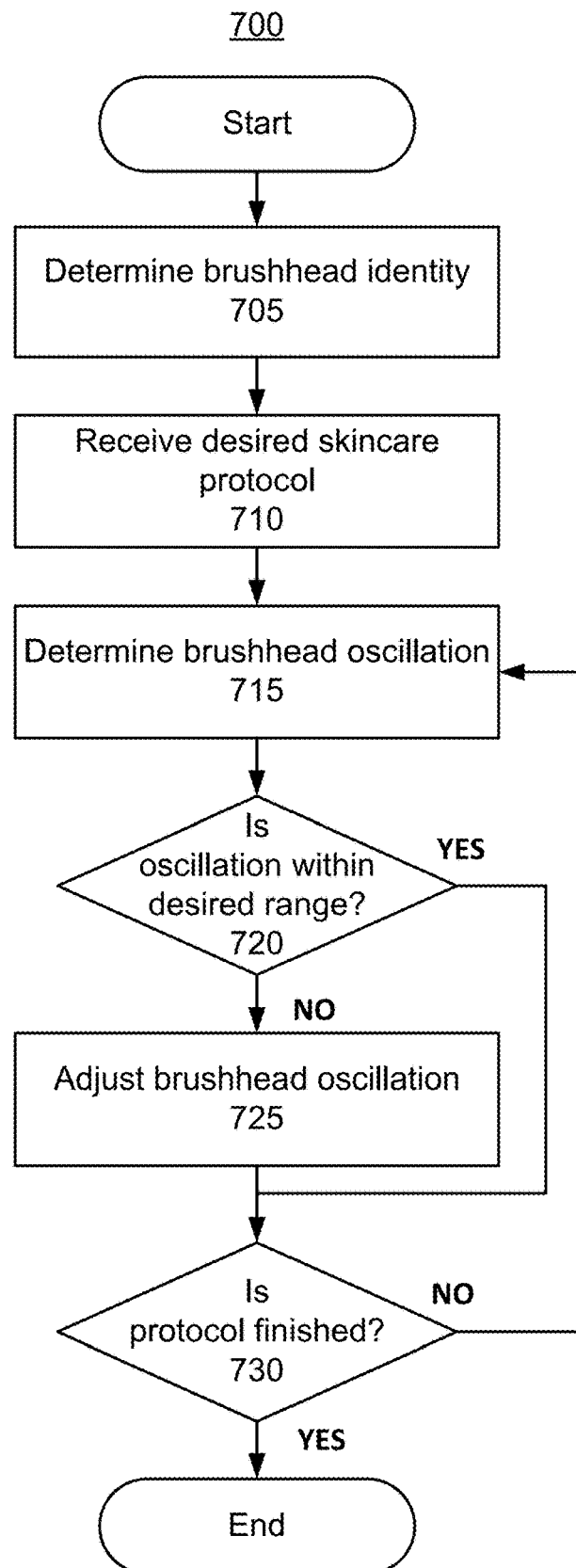
FIGS. 7A-7C are non-limiting examples of flow charts for a method of customizing performance of a skincare device, according to an embodiment of the present disclosure.

FIG. 7A a non-limiting example of a flow chart for a method 700 of optimizing performance of the device 100, according to an embodiment of the present disclosure. In step 705, the identity of the brushhead 120 is determined based on the marking 240. In step 710, the device 100 receives an input from the user for the desired skincare protocol or regimen to be executed. In step 715, the oscillation of the brushhead 120 is determined and monitored throughout the protocol. In step 720, the oscillation of the brushhead 120 is determined to be within or outside a desired range for the user-specified skincare protocol. In step 725, the brushhead 120 oscillation is adjusted if the oscillation is outside the desired range. In step 730, upon determining the protocol has not finished, the method 700 can return to step 715 and continue monitoring the brushhead 120 oscillation and adjusting the brushhead 120 oscillation upon determining the oscillation is outside the desired range.

Figure 7B:
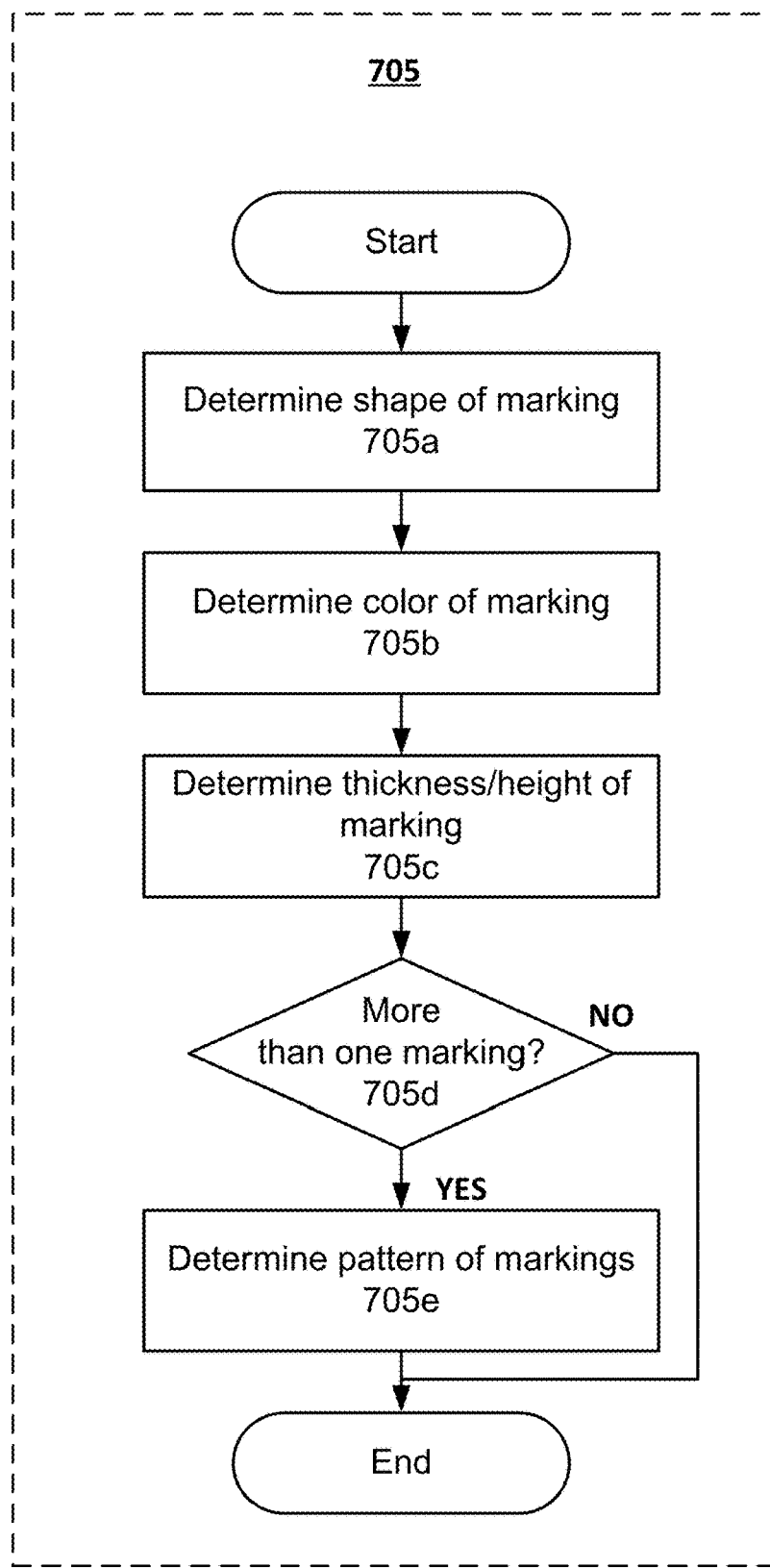

FIG. 7B a non-limiting example of a flow chart for a low-level expansion of the step 705 of the method 700 for optimizing performance of the device 100, according to an embodiment of the present disclosure. In step 705a, the shape of the marking 240 is determined. For example, the shape can be rectangular, triangular, circular, pentagonal, etc. In step 705b, the color of the marking 240 is determined via the first optical encoder 140. For example, the color of the marking 240 can be black, white, a gradient of black and white, or a color for the first optical encoder 140 having a visible-light detecting sensor. For example, the color of the marking 240 can be infrared reflective for the first optical encoder 140 having an infrared detecting sensor. For example, the color of the marking 240 can be UV reflective for the first optical encoder 140 having a UV detecting sensor. In step 705c, the thickness or height of the marking 240 can be determined. For example, the first optical encoder 140 determines the focal length between the first optical encoder 140 and a surface of the marking 240, and subsequently determines a difference between the focal length to the surface of the marking 240 and the focal length to a surface adjacent to the marking 240 (i.e. a reference surface). In step 705d, upon determining there is more than one marking 240, the pattern of the more than one shapes of the marking 240 is determined. The identity of the brushhead 120 can be determined by uniquely correlating a mixture of different more than one shapes of the marking 240, the color for each shape of the more than one shape of the marking 240, and the height for the each shape of the more than one shape of the marking 240. For example, an identifier pool including two shapes, two colors, and two thicknesses can result in a maximum of eight unique brushhead 120 identities when only using one marking 240. Increasing the pattern to two of the marking 240 can provide an additional 64 unique brushhead 120 identities. The identities of the various possible brushheads 120 can be stored in a look-up table on the device 100, the central device 620, or the external servers 642.

Figure 7C:
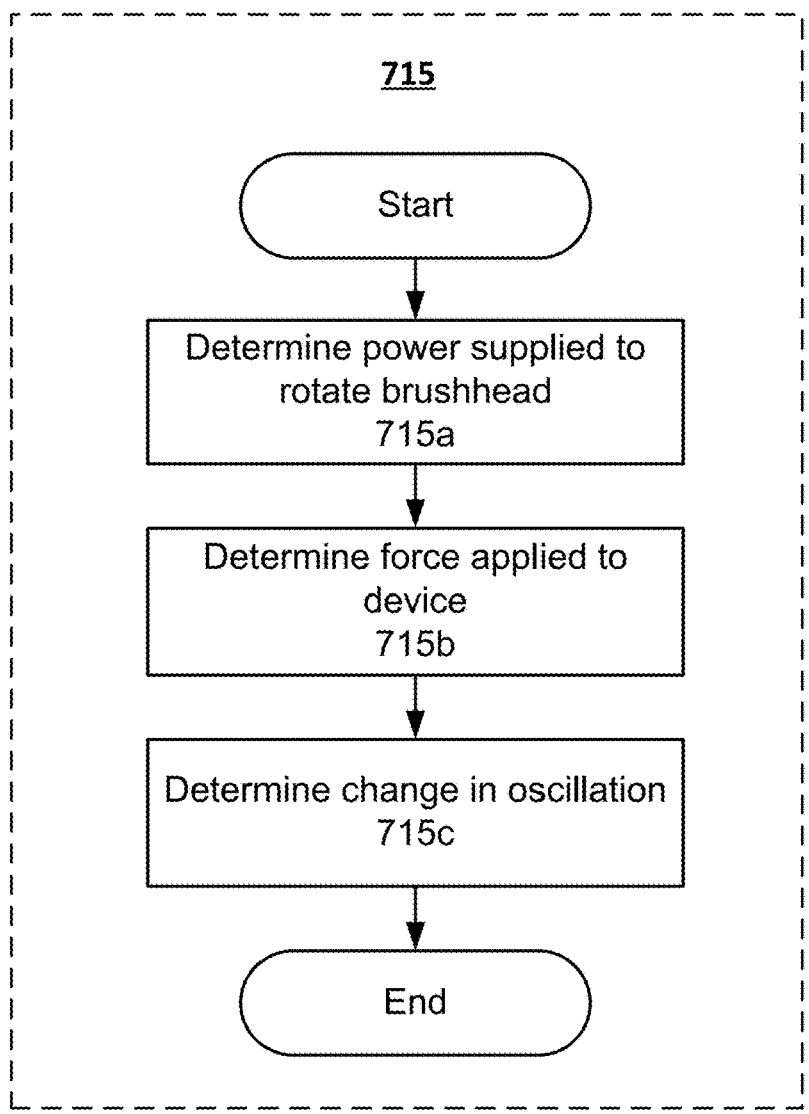

FIG. 7C is a non-limiting example of a flow chart for a low-level expansion of the step 715 of the method 700 for optimizing performance of the device 100, according to an embodiment of the present disclosure. In step 715a, the power supplied to the motor assembly 112 via the microcontroller or processor is determined. In step 715b, the force applied to the device 100, for example the force the user exerts to apply the device 100 to the user's skin, is determined via the force transducer 198. In step 715c, the change in the brushhead 120 oscillation is determined and subsequently used to adjust the power supplied to the motor assembly 112 to adjust the desired oscillation of the brushhead 120.

Figure 8:
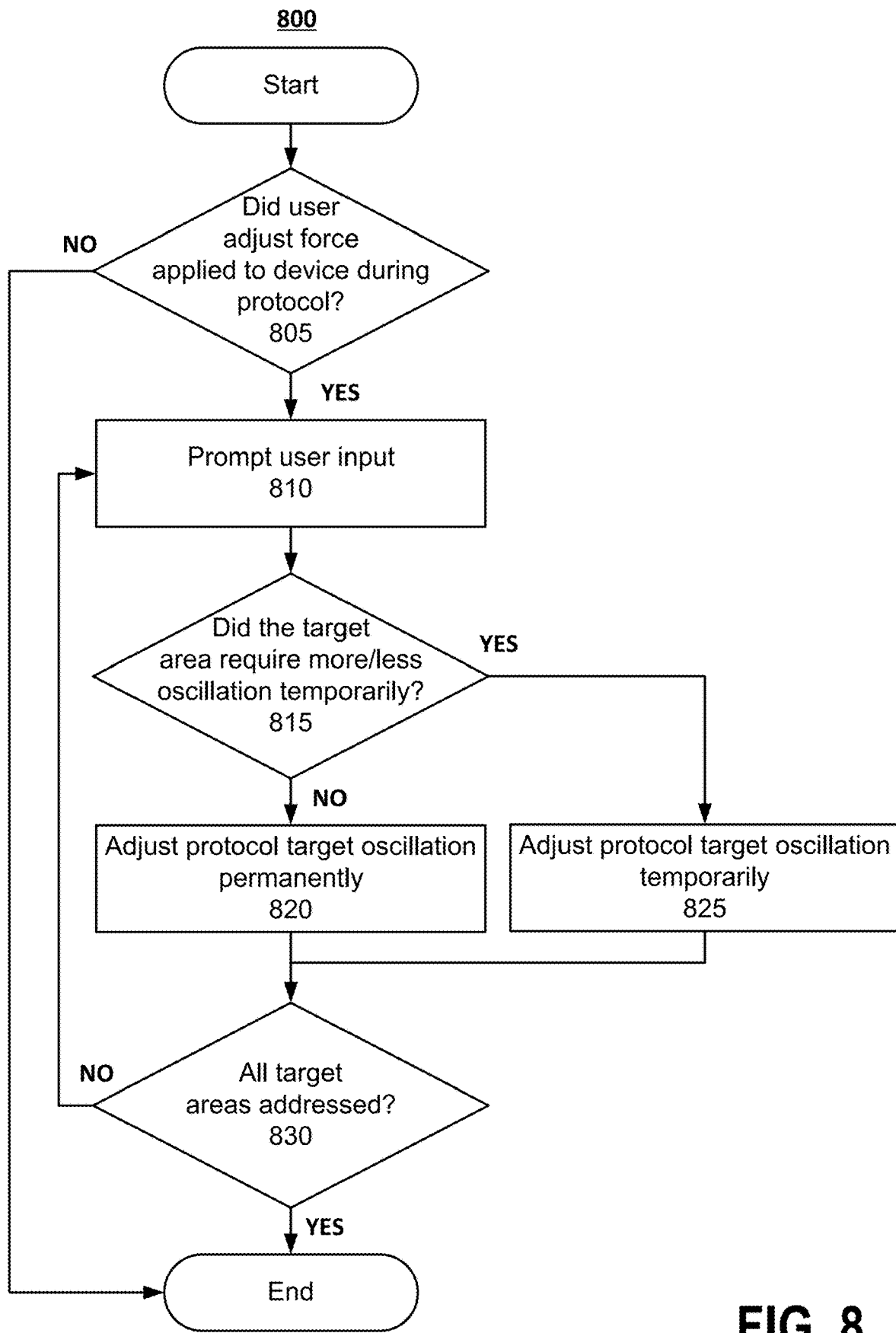
FIG. 8 is a non-limiting example of a flow chart for a method of customizing protocols for a skincare device, according to an embodiment of the present disclosure.

FIG. 8 is a non-limiting example of a flow chart for a method 800 for customizing skincare protocols of the device 100, according to an embodiment of the present disclosure. In step 805, it may be determined the user adjusted the applied force to the device 100 over a predetermined area. For example, the predetermined area may be a patch of skin including a sunburn or psoriasis. The location of the target patch of skin can be correlated with the change in applied force using the kinematic data and/or the second optical encoder 145 to track the location of the desired force adjustment. The selected skin care protocol or regimen can be similarly correlated. In step 810, user input is prompted to determine if the target area (i.e. the patch of skin) will benefit from a temporary or permanent oscillation adjustment. In step 820, the target area can be, for example, psoriasis and the protocol can be adjusted permanently. In step 825, the target area can be, for example, acne and recover after multiple days or weeks and the protocol can be adjusted temporarily. In step 830, upon determining the user adjusted the applied force in additional target areas, the method 800 can return to step 810 to prompt additional input from the user regarding the additional target areas.

The description above in connection with the appended drawings is intended as a description of various embodiments of the disclosed subject matter and is not necessarily intended to represent the only embodiment(s). In certain instances, the description includes specific details for the purpose of providing an understanding of the disclosed subject matter. However, it will be apparent to those skilled in the art that embodiments may be practiced without these specific details. In some instances, well-known structures and components may be shown in block diagram form in order to avoid obscuring the concepts of the disclosed subject matter.

Reference throughout the specification to "one aspect", "one embodiment", "an aspect", or "an embodiment" means that a particular feature, structure, characteristic, operation, or function described in connection with an embodiment is included in at least one embodiment of the disclosed subject matter. Thus, any appearance of the phrases "one aspect", "one embodiment", "an aspect", or "an embodiment" in the specification is not necessarily referring to the same aspect or embodiment. Further, the particular features, structures, characteristics, operations, or functions may be combined in any suitable manner in one or more aspects or embodiments. Further, it is intended that aspects or embodiments of the disclosed subject matter can and do cover modifications and variations of the described aspects or embodiments.

It must be noted that, as used in the specification and the appended claims, the singular forms "a," "an," and "the" include plural referents unless the context clearly dictates otherwise. That is, unless clearly specified otherwise, as used herein the words "a" and "an" and the like carry the meaning of "one or more." Additionally, it is to be understood that terms such as "upper," "lower," "front," "rear," "side," "interior," "exterior," and the like that may be used herein, merely describe points of reference and do not necessarily limit embodiments of the disclosed subject matter to any particular orientation or configuration. Furthermore, terms such as "first," "second," "third," etc., merely identify one of a number of portions, components, points of reference, operations and/or functions as described herein, and likewise do not necessarily limit embodiments of the disclosed subject matter to any particular configuration or orientation.

A number of embodiments have been described. Nevertheless, it will be understood that various modifications are made without departing from the spirit and scope of this disclosure. For example, preferable results are achieved if the steps of the disclosed techniques were performed in a different sequence, if components in the disclosed systems were combined in a different manner, or if the components were replaced or supplemented by other components.

The foregoing discussion describes merely exemplary embodiments of the present disclosure. As will be understood by those skilled in the art, the present disclosure may be embodied in other specific forms without departing from the spirit or essential characteristics thereof. Accordingly, the disclosure is intended to be illustrative, but not limiting of the scope of the disclosure, as well as the claims. The disclosure, including any readily discernible variants of the teachings herein, defines in part, the scope of the foregoing claim terminology such that no inventive subject matter is dedicated to the public.

The invention claimed is:

1. A method, comprising:
   determining a position of a skincare device with respect to a body part of a user via one or more sensors on the skincare device, the skincare device configured to apply a treatment to the user's body part;
   obtaining a location of a target area on the body part having a condition for application of the treatment;
   adjusting a parameter of the skincare device according to the location of the target area and based on the condition;
   upon determining the user changed force applied to the skincare device at the location of the target area, transmitting, via processing circuitry, a prompt to the user whether the user desires a temporary or permanent adjustment of the parameter at the target area; and
   adjusting, based on an answer to the prompt, the treatment at the target area.

2. The method of claim 1, wherein the one or more sensors are optical sensors configured to obtain images.

3. The method of claim 2, wherein determining the position of the skincare device further comprises:
   obtaining images via the one or more sensors as the skincare device is moved across the body part.

4. The method of claim 1, wherein the adjusted parameter of the skincare device is a power of the skincare device.

5. The method of claim 1, wherein the adjusted parameter of the skincare device is an oscillation frequency of a brushhead attached to a motor assembly in the skincare device.

6. The method of claim 5, wherein the skincare device includes a power supply electrically coupled to the motor assembly and adjusting the parameter of the skincare device further comprises adjusting a power delivered to the motor assembly from the power supply.

7. The method of claim 6, wherein the power supply is a battery.

8. The method of claim 1, wherein the one or more sensors include an inertial measurement unit (IMU) configured to measure kinematic data of the skincare device.

9. The method of claim 8, wherein the position of the skincare device is determined based on the measured kinematic data from the IMU.

10. The method of claim 9, wherein the one or more sensors further include an optical sensor configured to capture images.

11. The method of claim 10, wherein the one or more sensors further include a force transducer configured to measure the force applied to the skincare device.

12. The method of claim 11, wherein adjusting the parameter of the skincare device further comprises:
    upon determining the skincare device is positioned at the location of the target area, determining, via the force transducer, the force applied to the skincare device;
    determining whether the parameter of the skincare device is within a predetermined range based on the treatment; and
    upon determining the parameter of the skincare device is outside the predetermined range, adjusting the parameter of the device based on the force applied to be within the predetermined range.

13. The method of claim 1, wherein the skincare device includes a brushhead.

14. The method of claim 13, further comprising:
    determining an identity of the brushhead via the at least one sensor wherein the treatment is based on the identity of the brushhead.

15. The method of claim 1, further comprising: receiving a selection for the treatment from the user.

16. The method of claim 1, wherein the one or more sensors include one or more optical sensors configured to obtain images, the method further comprising:
    detecting, via processing circuitry, a presence of the condition in the obtained images; and
    adjusting the parameter of the skincare device based on the detected condition.

17. A skincare device, comprising:
    a brushhead;
    a body including a motor assembly configured to oscillate the brushhead;
    one or more sensors configured to determine a location of the brushhead relative to a body part of the user; and
    processing circuitry configured to:
        determine a position of the skincare device with respect to a body part of a user via the one or more sensors on the skincare device, the skincare device configured to apply a treatment to the user's body part;
        obtain a location of a target area on the body part having a condition for application of the treatment;
        adjust a parameter of the skincare device according to the location of the target area and based on the condition;
        upon determining the user changed force applied to the skincare device at the location of the target area, transmit a prompt to the user whether the user desires a temporary or permanent adjustment of the parameter at the target area; and
        adjust, based on an answer to the prompt, the treatment at the target area.

18. The device of claim 17, wherein the one or more sensors include an optical encoder configured to capture optical images, an inertial measurement unit (IMU) configured to determine kinematic measurements of the skincare device, and a force transducer configured to measure the force applied to the skincare device.

19. The device of claim 18, wherein the processing circuitry is further configured to upon determining the skincare device is positioned at the location of the target area, determine, via the force transducer, the force applied to the skincare device;
determine whether the parameter of the skincare device is within a predetermined range based on the treatment; and
upon determining the parameter of the skincare device is outside the predetermined range, adjust the parameter of the device based on the force applied to be within the predetermined range.

\* \* \* \* \*